United States Patent [19]

Friedman et al.

[11] 4,385,192
[45] May 24, 1983

[54] PROCESS FOR MANUFACTURING DBCP

[75] Inventors: Lester Friedman, Long Beach; Chester Callaway, Downey, both of Calif.

[73] Assignee: AMVAC Chemical Corporation, Los Angeles, Calif.

[21] Appl. No.: 922,097

[22] Filed: Jul. 5, 1978

[51] Int. Cl.$^3$ ............................................. C07C 17/02
[52] U.S. Cl. .................................... 570/252; 570/264; 570/116; 546/184; 423/470; 564/503; 544/107
[58] Field of Search ............. 260/652.5, 658 R, 654 D; 570/264, 252, 229, 116; 423/470; 564/503; 544/107; 546/184

[56] References Cited

U.S. PATENT DOCUMENTS

| | | | |
|---|---|---|---|
| 2,285,329 | 6/1942 | Columan et al. | 260/654 D |
| 2,364,588 | 12/1944 | Morris et al. | 260/652.5 R |
| 2,448,739 | 9/1948 | Ross | 260/658 R |
| 2,543,648 | 2/1951 | Strosacker et al. | 260/654 D |
| 2,989,570 | 6/1961 | Conrad et al. | 260/654 D |
| 3,268,597 | 8/1966 | Clemons et al. | 260/658 R |
| 3,325,476 | 6/1967 | Dowbenko | 564/503 |
| 3,481,982 | 12/1969 | Hennion | 546/184 |
| 3,497,555 | 2/1970 | Dudzenski | 564/503 |
| 3,876,712 | 4/1975 | Rains | 260/652.5 R |
| 4,032,584 | 6/1977 | Irani | 260/652.5 R |

FOREIGN PATENT DOCUMENTS

| | | | |
|---|---|---|---|
| 211196 | 5/1955 | Australia | 544/107 |
| 1443641 | 7/1971 | Fed. Rep. of Germany | 260/652.5 R |
| 985070 | 3/1965 | United Kingdom | 260/654 D |

*Primary Examiner*—Charles F. Warren
*Assistant Examiner*—Joseph A. Boska
*Attorney, Agent, or Firm*—Richard H. Zaitlen

[57] ABSTRACT

A process for manufacturing 1,2-dibromo-3-chloropropane is disclosed. The process comprises the steps of reacting bromine and allyl chloride at a temperature of from 5° to 85° C. and maintaining the reaction mixture between 60° to 90° C. for a sufficient length of time so as to permit the reaction between the bromine and allyl chloride to go to completion. In addition, the process also includes the step of adding an agent so as to stabilize and purify the product so formed.

5 Claims, No Drawings

PROCESS FOR MANUFACTURING DBCP

BACKGROUND OF THE INVENTION

1. Field of the Invention

This invention relates to the field of methods for manufacturing a chemical compound having special utility as a soil fumigant and nematocide.

2. Prior Art

The use of 1,2-dibromo-3-chloropropane (hereinafter referred to as "DBCP") as a soil fumigant and nematocide is well known. For example, as discussed in U.S. Pat. No. 3,049,472, one method for ridding the soil of nematodes which attack plant roots is by applying DBCP to the soil in specific proportions. Other patents which teach the use of DBCP as a soil fumigant and nematocide are U.S. Pat. Nos. 2,849,361; 2,849,363; and 2,849,367. However, while the use of DBCP as a soil fumigant and nematocide is well known, recently the method in which it has been made has come under close scrutiny. It has come to light that DBCP may be the causal factor involved in the temporary sterilization of males involved in the manufacturing of such product. In the past, DBCP has been prepared by merely adding bromine to allyl chloride at low temperatures. One reason why low temperatures were used was because higher temperatures caused the reactants as well as the DBCP to vaporize. On the other hand if the reaction temperatures are too low, the reactants will react only to a limited degree. While mixing bromine with the allyl chloride at low temperatures will produce crude DBCP, it does not yield a complete conversion of all the allyl chloride. This is extremely desirable inasmuch as allyl chloride is chemically reactive and has a low flash point. Thus, too much allyl chloride in the DBCP could render it flammable. On the other hand, the use of excess bromine leads to the production of undesirable polybrominated products and also necessitates the post-reaction removal of the excess bromine.

Thus, while prior art processes do teach the production of DBCP, they require additional steps after the DBCP is initially made whereby the various impurities present are removed. The present invention relates to a process which overcomes the shortcomings of the prior art in that the DBCP can be made in a safe and efficient manner, but without the complex purification steps required by prior art processes.

SUMMARY OF THE INVENTION

The process of the present invention relates to the manufacturing of DBCP, methods of purification, stabilization, as well as methods for coverting DBCP into a form which is more readily disposable. The process for producing DBCP comprises the steps of:

(a) reacting stoichiometric amounts of bromine and allyl chloride at preferred temperatures of from about 5° to 85° C.; and (b) maintaining the mixture so formed at a temperature of 60° to 90° C. for sufficient time to permit the reaction between the bromine and the allyl chloride to go to completion.

While the above-described process is most efficient in producing DBCP, a number of undesirable by-products and/or unreacted reactants remain in the DBCP so formed. To remove these undesirable compounds from the DBCP, the present invention adds an effective amount of a stabilization/purification agent. In one embodiment, the stabilization/purification agent comprises CaO, Ca(OH)$_2$ and mixtures thereof. In a second embodiment, the stabilization/purification agent comprises an agent of the formula:

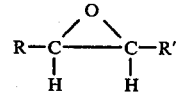

where R and R' are individually selected from the class consisting of H, alkyl radicals (C=1–20), substituted alkyl radicals, aryl radicals and substituted aryl radicals.

After the DBCP is produced, the present invention also teaches the step of subjecting DBCP vapors, filter cakes, or the liquid DBCP itself to an amine-containing agent. In this manner, the DBCP is converted into harmless substances (i.e. substances which do not adversely affect the environment) which are more readily disposable.

It is therefore one object of the present invention to provide an improved process for manufacturing DBCP.

Another object of the present invention is to provide a method for stabilizing and purifying DBCP after it is initially formed.

Yet another object is to provide a method for converting DBCP into a form which is readily disposable.

The novel features which are believed to be characteristic of the invention, both as to its organization and method of operation, together with further objectives and advantages thereof, will be better understood from the following description considered in connection with the accompanying examples in which presently preferred embodiments of the invention are illustrated. It is to be expressly understood, however, that the examples are for the purpose of illustration and description only, and are not intended as a definition of the limits of the invention.

DETAILED DESCRIPTION OF THE INVENTION

As discussed hereinabove, it is extremely desirable to develop a more efficient process for the manufacture of DBCP. DBCP has long been recognized as a very effected soil fumigant and nematocide. It was found that DBCP could be manufactured in almost quantitative yields and in a very high state of purity by reacting allyl chloride with bromine such that the amount of bromine to be used corresponds to the equimolar amount of allyl chloride present in the commercial material (i.e. the purity of the allyl chloride), and allowing the reaction to go to completion at an elevated temperature. In the preferred embodiment, the reaction between the allyl chloride and the bromine takes place at between 5° to 85° C., the preferred range being 70° to 80° C. The reaction mixture is then maintained at 70° to 90° C. for approximately ½ to 1 hour allowing the reaction to go to completion. While the above-noted process can be conducted as a batch or continuous process, since bromine and allyl chloride are low-boiling compounds and the heat of reaction is quite large, it is desirable to conduct the reaction in preformed DBCP. The preformed DBCP serves as a vehicle to achieve more effective heat transfer. In addition, using the preformed DBCP as the reaction medium helps lower the vapor pressure of the reactants. As a result, the reaction can be run more efficiently and rapidly.

A few examples of the above-described reaction will now be presented.

EXAMPLE I 237 grams of pure allyl chloride (3 gm-mole equivalents) are placed into a flask (500 ml) fitted with a thermometer, dropping funnel, dry-ice or brine cooled reflux condenser and a stirrer. The flask is cooled in an ice-salt bath. When the temperature of the allyl chloride drops to approximately 5° C., 480 grams of bromine (3 gm-mole equivalents) are added at such a rate that the temperature is kept below 20° C. for the first half of the reaction. During the addition of the balance of the bromine the reaction temperature is allowed to gradually rise to 60°–70° C., and by the end of the addition of the bromine the reaction temperature is between 75°–85°. This temperature is maintained for 30–60 minutes to complete the uptake of bromine and conversion of allyl chloride. The crude DBCP (715 gm, 99%) is a yellow to pale orange liquid which contains free hydrogen bromide. Analysis via gas chromatography indicates a DBCP content of approximately 96–98%.

EXAMPLE II

Into a flask (500 ml) fitted with a stirrer, thermometer, reflux condenser and two dropping funnels, is placed 100 grams of DBCP. The flask is cooled by a cold water bath, and the dropping funnels are filled respectively with allyl chloride (237 gm 97% pure) and bromine (480 gm). While the flask contents are mechanically stirred, allyl chloride and bromine are simultaneously added. The rates of addition are adjusted so that the allyl chloride/bromine ratio is 1:1.8 (by weight) or 1:0.58 (by volume), that is, a slight excess of allyl chloride is maintained until all of it has been added. The temperature of reaction is allowed to rise to 60°–70° by controlling the overall rate of addition of the reactants and the efficiency of the cooling bath. Towards the end of the reaction, the temperature is allowed to rise to 75°–80° and maintained there for 30–60 minutes to complete the reaction. The product is then cooled and analyzed. The crude DBCP has a purity of 96–98% and contains hydrogen bromide, but has no free bromine.

EXAMPLE III

A continuous reactor is constructed having a baffled residence tank joined to a pump. The pump is coupled to a heat exchange which in turn, flows back into the tank. A condenser and scrubber may also be joined to the tank so as to prevent the escape of harmful vapors. The process is started by filling the baffled residence tank with DBCP and circulating it through the system with a Teflon or Kynar coated circulating pump, preferably with a magnetically coupled drive. Allyl chloride (97%) and bromine are metered into the system with accurate metering pumps in the weight ratio of 1:2.025 or in the volume ratio of 1.0:0.609. The reaction temperature is maintained between 75°–85° C. by use of the heat exchanger. A residence time of 30 minutes at reaction temperatures of 70°–90° C. is optimum. The DBCP formed is collected as it overflows from the residence tank. The ratio of recirculated DBCP to allyl chloride and bromine can vary from 3 to 10 or more depending upon the size of the heat exchanger and the temperature of the coolant used in the heat exchanger.

PURIFICATION AND STABILIZATION STEPS

As discussed hereinabove, notwithstanding the improved efficiency of the process, the crude DBCP formed contains hydrogen bromide and other acidic impurities. In fact, it is believed that in all prior art processes such acidic impurities are present. In the past, these have been removed by the use of an aqueous or solid caustic wash. None of these prior art methods is wholly satisfactory. The aqueous wash yields a wet product which must be dried prior to storage and packaging. This is because even small amounts of water in the DBCP tends to substantially decrease its stability. While solid caustic is more effective, as it is used it becomes less effective and becomes slimy thereby adversely affecting the process equipment. Further, notwithstanding the fact that caustics have been used, all are not effective. For example, sodium and potassium carbonate will remove hydrogen bromide from the liquid DBCP, and will yield a neutral product, but colored bodies remain in the DBCP. The present invention teaches that slaked lime [$Ca(OH)_2$] can be used for purification and stabilization of DBCP and overcomes the problems associated with the prior art. In the preferred embodiment, $\frac{1}{8}$–$\frac{1}{2}$% by weight, and more preferably $\frac{1}{4}$–$\frac{1}{2}$%, of the agent has been found to be effective in converting crude DBCP to pure technical grade stable material.

It should be noted that in order to store, package and market DBCP, it must be free from all acidic impurities and water. Removal of these impurities and the water enables the DBCP to remain stable for reasonably long periods of time. The use of the $Ca(OH)_2$ not only removes substantially all the acidic impurities, it also dries the product and decolorizes it. In addition to the use of $Ca(OH)_2$, it has also been found that lime (CaO) in the same amounts can be used. However, greater effectiveness is achieved by using a mixture of CaO and $Ca(OH)_2$ in the ratio of 1:2 weight to weight. While the amount of CaO to $Ca(OH)_2$ is not critical, in order to obtain good results the amount of CaO should be present at a level of at least 10% by weight. In the process of the present invention, since the reaction time with $Ca(OH)_2$ is extremely rapid, DBCP can be purified by using a bed or layer of $Ca(OH)_2$ in a filter or by profusion through a column. Further, with respect to Example 3 above, the $Ca(OH)_2$ and CaO can be used in a cartridge or cylindrical container and the crude DBCP passed therethrough. After a predetermined length of time, the cylinder or cartridge is removed and a new cylinder containing fresh material substituted in its place. Thus, there are a number of different systems by which the $Ca(OH)_2$ and/or the CaO can be used to contact the crude DBCP so as to purify and stabilize it.

A few examples showing the use of $Ca(OH)_2$ and/or CaO are set forth below.

EXAMPLE IV

To the crude orange-yellow DBCP (20° C.) made in Example I, 3.5 gm of $Ca(OH)_2$ were added. The mixture was stirred for a few minutes and filtered with the aid of a Buchner funnel. An essentially colorless filtrate of purified DBCP (96–98%) was formed. The purified DBCP was analyzed and found to be acid-free and stable. A white powdery filter cake was left on the funnel.

In a similar manner, crude DBCP from examples II and III were heated prior to the introduction of the Ca(OH)₂. Good results (i.e. essentially colorless and acid-free DBCP) were likewise obtained. The Ca(OH)₂ can also be added to the crude DBCP prior to cooling.

EXAMPLE V

To further remove water from the DBCP in order to further stabilize this compound, the crude DBCP (20° C.) was treated with the combination of Ca(OH2)₂ and CaO in the following manner. To the crude DBCP formed in Example I, 2.33 gm of Ca(OH2)₂ and 1.71 gm of CaO were added. The CaO acted as a drying agent and also aided in the removal of any free acid. The resulting DBCP formed was a clear, almost colorless acid-free liquid.

It is believed that the reaction between the Ca(OH)₂, CaO and the HBR or equivalent acid present is as follows:

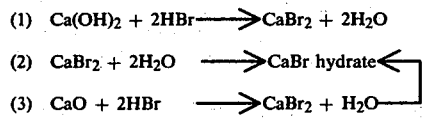

(1) $Ca(OH)_2 + 2HBr \longrightarrow CaBr_2 + 2H_2O$ (2) $CaBr_2 + 2H_2O \longrightarrow CaBr\ hydrate$ (3) $CaO + 2HBr \longrightarrow CaBr_2 + H_2O$ When the DBCP is purified with Ca(OH)₂ and/or CaO, the resulting CaBr₂ hydrate is easily removed by filtration (centrifugation). This can lead to the production of a filter cake containing at least trace amounts of DBCP. In addition to the filter cake, some DBCP vapors are also produced. In the past, conversion of the DBCP (in liquid or vapor form) to a harmless substance was a problem. Because of the health problems believed to be related to DBCP, prior art processes used complex processing techniques. The present invention provides a solution to this problem. For example, material from the filter cake is destroyed by quenching it with diethanolamine in dimethylformamide (DMF) 1:1 weight to weight.

While a wide range of potential candidates exist for converting DBCP into a harmless substance, the use of an amine has been found to be particularly quick and efficient. By the use of an amine the DBCP undergoes dehydrohalogenation as follows:

(4) $BrCH_2\ CHBr - CHCl \longrightarrow$

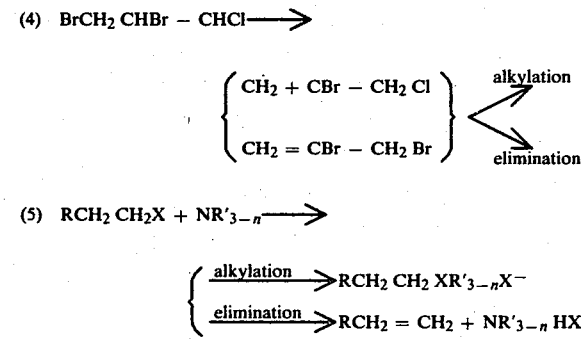

(5) $RCH_2\ CH_2X + NR'_{3-n} \longrightarrow$ $\begin{cases} \xrightarrow{\text{alkylation}} RCH_2\ CH_2\ XR'_{3-n}X^- \\ \xrightarrow{\text{elimination}} RCH_2 = CH_2 + NR'_{3-n}\ HX \end{cases}$ wherein R and R' are each selected from the group consisting of H, alkyl (C=1-20) radicals and aryl radicals, n=0, 1, 2, or 3 and X=halogen. While all amines are within the scope of the present invention, for a variety of reasons certain amines, while effective, are not preferred. For example, ammonia has been found to be effective, but has an unpleasant smell. Likewise diethylamine and triethylamine have been found to be effective, but because of their low boiling point and low flash point are not preferred. Compounds have been found to be effective include, for example, piperidine, triethanolamine, propylenediomene, ethylene, diamine, ethanolamine, diethanolamine, triethanolamine, aniline, iso, dris and triso propanolamine, and benzylamine, and polyamines such as triethylene tetramine. Thus it can be seen that aliphatic and aromatic compounds as long as they contain an amine group are within the scope of the present invention.

Of the above amines, the following possesses a combination of characteristics which have been found to be particularly desirable for use in converting the DBCP into a harmless substance. These characteristics include, for example, the production of a compound that can be flushed into the sewer system, relatively inexpensive, low flash point, and not requiring the use of complex processing equipment: morpholine, diethanolamine, and piperidine. These amines are preferably used in a water miscible solvent such as DMF, dimethylacetaimide (DMAc), n-methylpyrrolidone, pyrrolidone, tetramethylurea, dipropylene glycol or propylene glycol. While other solvents such as kerosene, xylene, hexane and the like can be used, such solvents are water immiscible, and/or flammable and therefore not preferred.

In view of the above, the specific amount of amine to be used is determined on the amount of DBCP present. Obviously the greater the quantity of DBCP to be converted, the greater the amount of amine which would have to be used. In the preferred embodiment, to insure that no DBCP remains in the filter cake, or in any waste liquid DBCP or vapors, excess amine is used.

It has been found that purifying and stabilizing DBCP using any caustic, even Ca(OH)₂ and CaO discussed hereinabove, tends to leave some residues behind which ultimately can contaminate the DBCP. In view of the hazards and restrictions involved in the handling of DBCP, it is extremely desirable to develop a process such that the residue problem could be avoided. In the second embodiment, organic oxides such as ethylene oxide, propylene oxide, styrene oxide, epoxized soybean oil, epichlorohydrin and the like in an amount of ⅛ to ½ wt percent (preferably ¼ to ½) have been found to effectively neutralize and stabilize the crude DBCP to give a product requiring no further handling. In other words, no residues are formed and nothing additional need be added in order to decontaminate the DBCP. Because of its ease of handling and cost, propylene oxide is the preferred compound. When added to crude DBCP at a level of ⅛-½ weight percent (preferably ¼ to ½) at a temperature of between 40°-90° C., the propylene oxide reacts substantially instantaneously with all the acidic impurities, and in addition decolorizes the product. The resulting DBCP is neutral and almost water white. While the preferred reaction temperature range is 40°-70° C., lower reaction temperature will work but are not recommended since there appears to be a threshold below which the reaction of propylene oxide with the acidic impurities either does not take place or is extremely slow. Higher reaction temperatures are not required. It has been determined that the preferred organic oxides are those having the following formula.

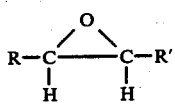

where R and R' are individually selected from the class consisting of H, alkyl radicals (C=1–20), substituted alkyl radicals, aryl radicals and substituted aryl radicals.

EXAMPLE VI

To the crude DBCP (20° C.) from Example I, 3 gm. of propylene oxide are added. After thirty minutes a sample is taken (5 ml) and shaken with 10 ml of water and tested for acidity using a pH meter. The sample was found to be somewhat acidic. The mixture was then heated to 60° C. where upon the coloration of the liquid tended to become clear to pale yellow. Another sample was taken and tested for acid. The product was found to be acidfree.

EXAMPLE VII

Example I was repeated, but prior to cooling, 3.8 gm of propylene oxide were added. After thorough mixing, a sample was taken and tested for acid and it was found to be acid-free.

In a similar manner, ethylene oxide, butylene oxide, epychlorohydrine, styrene oxide, epoxized soybean oil were added to crude DBCP. The mixture was heated to temperatures in the range of 40°–90° C. and then tested for acid by the use of a pH meter. The DBCP was found to be essentially colorless and acid-free.

It is believed that the reason why such oxide compound removes the acid is based on the following reaction:

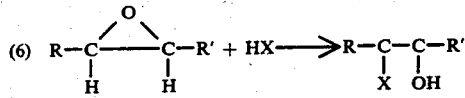

Although this invention has been disclosed and described with reference to particular embodiments, the principals involved are susceptible of other applications which will be apparent to persons skilled in the art. This invention, therefore, is not intended to be limited to the particular embodiments herein disclosed.

What is claimed is:

1. A process for manufacturing DBCP comprising the steps of:
   (a) reacting bromine and allyl chloride at a temperature of from 5° to 85° C.; and
   (b) maintaining the mixture so formed at a temperature of at least 60° to 90° C. for sufficient time to permit the reaction between the bromine and allyl chloride to go to completion thereby forming DBCP; and
   (c) adding an effective amount of epoxized soybean oil as a stabilization/purification compound to the DBCP formed in step (b) while maintaining the DBCP at a temperature of from 40° to 90° C. whereby acidic impurities in said DBCP are caused to react with said compound.

2. A process for manufacturing DBCP according to claim 1 wherein said mixture is maintained at said temperature range in step (b) for about ½ to 1 hour.

3. A process for manufacturing DBCP according to claim 1 wherein the reaction between the bromine and the allyl chloride takes place in the presence of preformed DBCP.

4. A process for manufacturing DBCP according to claim 1 wherein stoichiometric amounts of bromine and allyl chloride are used in step (a).

5. A process for manufacturing DBCP according to claim 1 wherein said epoxized soybean oil is present in an amount of ¼ to ½% by weight of the DBCP.

* * * * *